United States Patent
Cave et al.

(10) Patent No.: US 11,083,846 B2
(45) Date of Patent: Aug. 10, 2021

(54) ERGONOMIC SLIDE SYRINGE

(71) Applicant: GlaxoSmithKline Consumer Healthcare (UK) IP Limited, Brentford (GB)

(72) Inventors: George Cave, Warwickshire (GB); Paul Richard Draper, Warwickshire (GB); Daniel Paul Salisbury, Warwickshire (GB)

(73) Assignee: GlaxoSmithKline Consumer Healthcare (UK) IP Limited, Brentford (GB)

( * ) Notice: Subject to any disclaimer, the term of this patent is extended or adjusted under 35 U.S.C. 154(b) by 126 days.

(21) Appl. No.: 15/770,810

(22) PCT Filed: Oct. 28, 2016

(86) PCT No.: PCT/IB2016/056527
§ 371 (c)(1),
(2) Date: Apr. 25, 2018

(87) PCT Pub. No.: WO2017/072728
PCT Pub. Date: May 4, 2017

(65) Prior Publication Data
US 2018/0311441 A1    Nov. 1, 2018

Related U.S. Application Data

(60) Provisional application No. 62/248,386, filed on Oct. 30, 2015.

(51) Int. Cl.
*A61B 5/315* (2021.01)
*A61M 5/31* (2006.01)
*A61M 5/315* (2006.01)

(52) U.S. Cl.
CPC ...... *A61M 5/3129* (2013.01); *A61M 5/31511* (2013.01); *A61M 2005/31518* (2013.01); *A61M 2205/586* (2013.01)

(58) Field of Classification Search
CPC ............ A61M 5/3129; A61M 5/31511; A61M 2005/31518; A61M 2205/586
(Continued)

(56) References Cited

U.S. PATENT DOCUMENTS 2,134,144 A    10/1938    Pincock
3,325,061 A    6/1967    Ellsworth
(Continued)

FOREIGN PATENT DOCUMENTS

CH    661444 A5    7/1987
EP    2570145 A1    3/2013
(Continued)

*Primary Examiner* — Phillip A Gray
(74) *Attorney, Agent, or Firm* — Roshni A. Sitapara

(57) ABSTRACT

Disclosed are syringes that allow one-handed operation for measuring and dispensing a medicament, provide consistent finger placement on the syringe barrel. The syringes have a generally oval exterior shape that comfortably fits a user's hand and prevents rolling of the syringe when placed on a surface. Due to the shape of the syringes, the dispensing tip will not touch a surface or substrate when the syringe is placed thereon, providing improved hygiene and reduced contamination. The syringes preferably have a dosage marking on the barrel that provides ease of seeing the withdrawn medicament. The dosage marking can be raised and/or colored and/or made light sensitive. The raised markings can provide an audible and/or tactile indication of the dose of medicament drawn into or out of the syringe.

17 Claims, 4 Drawing Sheets

(58) Field of Classification Search
USPC .......................................................... 604/187
See application file for complete search history.

(56) References Cited

U.S. PATENT DOCUMENTS

| | | | | | |
|---|---|---|---|---|---|
| 3,786,811 | A | * | 1/1974 | Holbrook | A61M 5/3129 |
| | | | | | 604/218 |
| 4,610,666 | A | | 9/1986 | Pizzino | |
| 5,163,907 | A | | 11/1992 | Szuszkiewicz | |
| 8,888,751 | B2 | * | 11/2014 | Mudd | A61M 5/3158 |
| | | | | | 604/218 |
| 2007/0088285 | A1 | * | 4/2007 | Sharp | A61M 5/31525 |
| | | | | | 604/187 |

FOREIGN PATENT DOCUMENTS

| | | |
|---|---|---|
| WO | WO0147584 A1 | 7/2001 |
| WO | WO2012020957 A2 | 2/2012 |

* cited by examiner

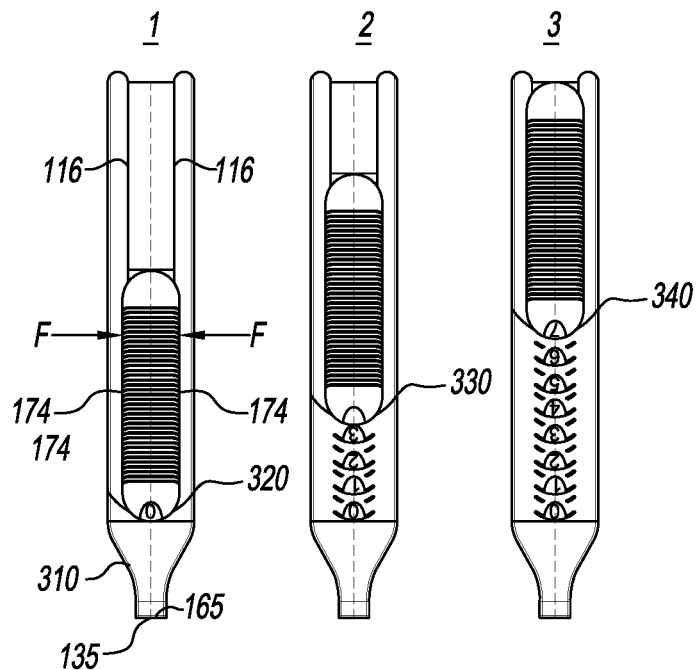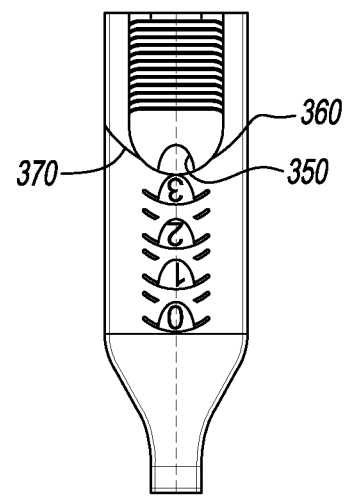
FIG. 3A  FIG. 3B
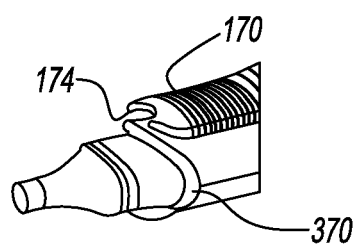
FIG. 3C

ERGONOMIC SLIDE SYRINGE

This application is a 371 of International Application No. PCT/IB2016/056527, filed Oct. 28, 2016, which claims the benefit of U.S. Provisional Application No. 62/248,386, filed Oct. 30, 2015, which is incorporated herein in its entirety.

CROSS-REFERENCE TO RELATED APPLICATIONS

This application claims the benefit of U.S. Provisional Application No. 62/248,386 filed Oct. 30, 2015, the contents of which are hereby incorporated herein by reference in its entirety.

BACKGROUND OF THE DISCLOSURE

1. Field of the Disclosure

The present disclosure relates generally to slide syringes. More particularly, the present disclosure relates to an ergonomic syringe and method for manufacturing same as well as methods of measuring and dispensing a medicament from the syringe using one hand of the user.

2. Description of Related Art

Syringes are used to inject and/or withdraw fluids in, for example, laboratory and medical administration. Throughout the descriptions herein, reference is made to a proximal end and a distal end of a syringe. Proximal end is the end closer to a user's (i.e., operator's) body when operating a syringe. Distal end is the end furthest from the user's body from which fluid either exits, during dispensing, or enters, during withdrawal from an external source, the syringe.

A syringe typically has two or more parts. One part is a cylindrical barrel that normally has a substantially hollow interior. Another part is a plunger that fits in the hollow interior of the barrel. The plunger either pushes fluid or medicament out of the barrel during injection, or pulls fluid into the barrel during withdrawal from a source.

Many syringes have a hollow needle or cannula permanently or detachably connected at the distal end of the barrel. For syringes that do not have a hollow needle or cannula, these syringes have a fill and dispense opening that is generally part of the body of the syringe. These latter syringes are frequently used for dispensing medicaments orally to a patient in need of such medicaments.

Dispensing medicament from a syringe is normally accomplished by pushing the plunger in the hollow interior of the barrel toward the distal end, where the medicament is located. This action reduces both the volume and force needed to expel the medicament from the hollow interior of the barrel. Drawing a medicament from an external source into the syringe is accomplished by partially drawing the plunger from the barrel to create a vacuum. This action causes medicament to flow from the external source into the barrel.

Syringe plungers generally have a flange at the proximal end thereof. In conventional use, a user holds a surface of the plunger flange to exert force to withdraw the plunger from the barrel or to push the plunger further into the barrel. Some syringes have a flexible, elastomeric member, referred to as a seal, which fits around the plunger near the distal end of the plunger and facilitates the creation of the vacuum as a user withdraws the plunger from the barrel. Typically, syringes have markings on the barrel that signify a quantity of medicament therein.

For many syringes, various techniques and hand positions are needed to move the plunger to create the vacuum that withdraws medicament from an external source and/or to move the plunger to expel the medicament. Conventionally, a user employs two hands. In particular, the user grasps the outer surface of the barrel with one hand, and grasps the plunger flange with the other hand. However, this two-handed technique has several disadvantages. For example, the user does not have a hand available to stabilize either the patient's body or the vial containing the medicament being withdrawn.

Further, if one has limited hand/finger dexterity and/or strength, such as one with arthritis, or one is administering to an infant or young child, the ability to use both hands is limited. Thus, a syringe directed to one-hand use technique is particular useful for both situations.

Accordingly, there is a need for an ergonomic syringe that can be used with one hand that accounts for limited hand/finger dexterity and/or strength, and/or is helpful for administering to infants and young children.

SUMMARY OF THE DISCLOSURE

The present disclosure provides a syringe or syringe device and a method for making the syringe, and for use of the syringe by the user employing one hand.

The present disclosure also provides such a syringe that is comfortable to hold, and maintains cleanliness of the dispensing tip due to the syringe's ergonomic design when placed on a surface or substrate.

The present disclosure further provides such a syringe that assures ease of delivery of the correct dosage of the medicament in the syringe.

In one embodiment of the present disclosure, there is provided a syringe that comprises a substantially oval barrel and a plunger slide assembly. The barrel has a body with a hollow interior along its major or longitudinal axis that extends between a proximal end and a distal end thereof. The body has a body slot or opening in a portion thereof that extends from the proximal end to about one-half the length of the body. The barrel has a tip portion that tapers from the distal end of the body to a substantially circular fill and dispense opening. The plunger slide assembly has a plunger tip disposed at the distal end of the plunger that tapers to correspond to the interior dimension of the tip portion of the barrel body. The plunger tip ends at the substantially circular fill and dispense opening. The plunger slide assembly has a longitudinal axis with a first portion thereof attached to the plunger and is adapted to fit in the body slot or opening, and a second portion configured to be disposed above the outer surface of the barrel body along the body slot or opening. The second portion is configured to be slightly wider than the dimension of the body slot or opening such that the lateral edges of the second portion are supported by the lateral edges of the slot or opening.

The present disclosure also provides that the barrel body has a set of substantially evenly spaced dose markings disposed on a surface of the barrel between the body slot and the tip portion of the barrel. The second portion of the plunger slide assembly has an end that corresponds to the set of substantially evenly spaced dose markings disposed on the surface of the barrel.

The present disclosure further provides that the dosage markings can be raised above the outer surface of the barrel.

The present disclosure still further provides that the dosage markings can be colored for ease of viewing.

The present disclosure yet further provides that the dosage markings can be colored with a light-sensitive substance to provide luminescence in the dark.

The present disclosure also provides that the plunger has a grip on the second portion thereof, and the distal end of the grip has a protrusion that interacts with the raised dosage markings of the barrel to provide an auditable and/or tactile "click" that ensures the user has drawn the proper amount of medicament.

The present disclosure further provides that the grip has one or more ridges that provide a surface against which a user can push and pull with a finger, such as a thumb.

The present disclosure also provides an embodiment in which the plunger distal end of the grip has an end that includes a "window" so that a user can more clearly see the dose that has been drawn by retraction of the plunger into and through the dispense opening.

The present disclosure also provides an embodiment in which the seal is colored and the barrel is transparent or translucent to a certain degree such that the seal provides a further indication that a user can see the dose that has been drawn by retraction of the plunger into and through the dispense opening.

In another embodiment, the present disclosure provides a method of producing a syringe. The method comprises providing a syringe body having a hollow cross-section and a plunger. The method further comprises providing the body with a substantially oval barrel having a longitudinal or major axis and a perpendicular minor axis, and having a length between a proximal end and a distal end, providing a body slot disposed in the barrel along the longitudinal axis in which the body slot has a length and a width, and the length is measured from the proximal end towards the distal end for about one-half the length of the barrel, and the width is smaller than the longitudinal or major axis and is approximately centrally disposed perpendicularly to the minor axis, and providing a body tip portion that tapers from the distal end of the barrel to a substantially circular fill and dispense opening.

The method further comprises providing a substantially oval plunger body having a proximal end and a distal end, and providing the plunger body with exterior dimensions that correspond to the hollow cross-section of the substantially oval barrel, providing on the plunger body a plunger tip disposed at the distal end of the plunger body and tapering in dimension to correspond to the hollow cross-section of body tip portion, and ending substantially at the dispense opening of the barrel, and providing on the plunger body a plunger grip having a length and a width with a first end of the length of the plunger grip attached to the proximal end of the plunger body and a second end of the length of the plunger grip configured to be disposed above the surface of the barrel. The plunger grip is sized so that a part of the plunger grip remains disposed above the body slot. This configuration will be discussed in more detail in conjunction with the Figures.

Further, the method comprises that the plunger grip can be provided with a set of substantially evenly spaced ridges disposed on an upper surface of the plunger grip to provide a surface against which a user can push and pull with a finger, such as a thumb.

The present disclosure also provides that the method can include providing the plunger grip with a protrusion that interacts with the raised dosage markings of the barrel to provide an auditable and/or tactile "click" that ensures the user has drawn the proper amount of medicament into the syringe body.

The present disclosure also provides that the method can include providing the plunger grip portion with a distal end that includes a "window" so that a user can more clearly see the dose that has been drawn by retraction of the plunger into and through the dispense opening into the syringe body.

Based upon the foregoing, the present disclosure provides ergonomic syringes that have improved user control and stability when exerting force needed to move the plunger. The ergonomic design reduces the overall range of motion that the finger must travel to use the syringe and provides consistent finger placement on the syringe barrel.

The above-described and other advantages and features of the present disclosure will be appreciated and understood by those skilled in the art from the following detailed description, drawings, and appended claims.

BRIEF DESCRIPTION OF THE DRAWINGS

FIG. 3A shows the syringe of FIG. 1 in three varying degrees of withdrawal, namely 3A1, 3A2 and 3A3, of the plunger from the barrel.

FIG. 3B is an enlarged view of the markings and the end of the plunger grip portion having a window of the syringe of FIG. 1.

FIG. 3C is a close up view of the shape, window and seal on the plunger of the syringe of FIG. 1.

DETAILED DESCRIPTION OF THE DISCLOSURE

Figure 1:
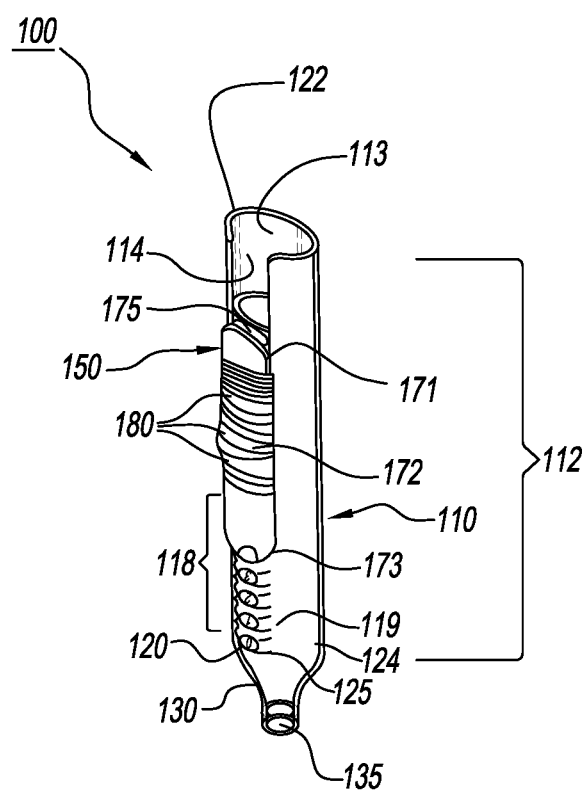
FIG. 1 is a side perspective view of an embodiment of a syringe according to the present disclosure in a partially retracted position.
Figure 2A:
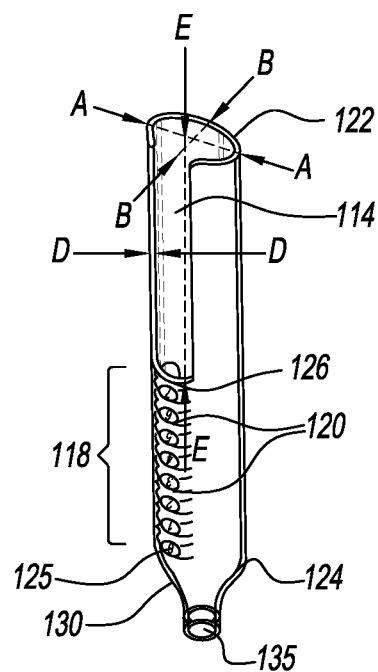
FIGS. 2A and 2B are exploded views of a barrel and plunger of the syringe of FIG. 1.

Referring to the drawings and in particular to FIG. 1, an exemplary embodiment of a syringe of the present disclosure is generally referred to by 100. Syringe 100 includes a barrel 110 and a plunger 150. Barrel 110 has a body 112 with a hollow interior 113 that extends in a longitudinal axis from a proximal end 122 to a distal end 124, and an integrally formed tip or tip portion 130. Body 112 has a substantially hollow interior and, as shown in FIG. 2A, preferably has a substantially oval or elliptical shape. Body 112 has a major or longitudinal axis across lines A-A and a minor axis across lines B-B (see, FIG. 2A). Major axis A-A and minor axis B-B are disposed perpendicular to each other.

Body 112 includes an elongated body slot 114 formed through a wall of the body from proximal end 122 to about half way toward distal end 124. Body 112 has a portion 118 from distal end 124 to body slot 114 that is the remainder of body 112. Portion 118 is integrally formed and contiguous with tip portion 130. Tip portion 130 preferably has a circular or oval shape and terminates in a dispense opening 135.

Portion 118 has an outer surface 119 with a plurality of dosage markers 120. Dosage markers 120 are disposed substantially in alignment with body slot 114.

Plunger 150 has a substantially oval plunger body 160, a plunger tip or tip portion 165 (shown clearly in FIG. 2B) and a plunger grip portion 170. Plunger body 160 can easily be inserted into body slot 114 and slid along the length of barrel 110 from proximal end 122 toward distal end 124, and vice versa, namely to and from the beginning and end of body slot 114. Plunger body 160 has an outer dimension that is slightly less than the inner dimension of hollow interior 113 of body 112. Plunger tip 165 has an outer dimension, shown clearly in FIG. 2B, that substantially corresponds to the inner dimension of tip portion 130.

In the embodiment shown in FIG. 1, body 112 is substantially transparent or translucent so that dosage markers 120, and the actual dosage of medicament drawn in dispensing opening 135, can be more clearly seen. Body 112 is preferably made of a thermoplastic material that provides for a certain degree of flexibility so that plunger body 160 can be more easily inserted into opening 135 and slide along the length of barrel 110 from proximal end 122 toward distal end 124.

Figure 2B:
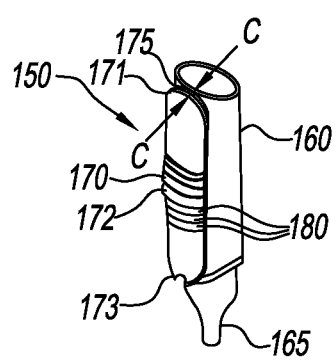

Referring to FIGS. 1 and 2B, plunger grip portion 170 is connected at one end to plunger body 160 via a connection 175. Connecting plunger grip portion 170 to plunger body 160 at one end using connection 175 provides plunger grip portion 170 with a configuration similar to that of a pocket clip on a pen. In addition, referring to FIG. 2B, the thickness, line C-C, of connection 175 is approximately equal to the thickness, line D-D, of body 112. Plunger grip portion 170 includes a plurality of step-like, evenly spaced ridges 180 that increase in height from a first end 171 of plunger grip portion 170 to the approximate center 172 of plunger grip portion 170 and then decrease in height from the approximate center 172 to a second end 173 of plunger grip portion 170. The increasing and then decreasing height of ridges 180 provide for a configuration of plunger grip portion 170 that can be easily pulled away from tip portion 130 to draw medicament into syringe 100 through dispense opening 135, and easily pushed toward tip portion 130 to dispense medicament through dispense opening 135. Of course, plunger grip portion 170 can be attached to plunger body 160 at more than one end, e.g., along all or a portion of the length plunger body, so long as the attachment does not interfere with the movement of plunger 150 in body slot 114. Though shown as a series of attached increasing and then decreasing ridges 180, plunger grip portion 170 can also be configured as a series of separate ridges with spaces therebetween. Alternatively, plunger grip portion 170 could also be configured as a "roughened" surface. All that is required is that plunger grip portion 170 provide a surface such that a user's finger, e.g. thumb, has a surface that can push/pull plunger grip portion 170 toward/away from distal end 124.

Referring to FIGS. 2A and 2B, body slot 114 has a length and plunger grip portion 170 has a length from first end 171 to second end 173. Thus, plunger grip portion 170 aligns with dosage marker 125 (i.e., 0 mL) disposed closest to tip portion 130 when plunger 150 is inserted in hollow interior 113 and fully slid through body slot 114 toward distal end 124, and also aligns with dosage marker 126 furthest from tip portion 130 when plunger 150 is drawn away from tip portion 130 to provide the maximum dose of medicament (i.e., 7.0 mL shown in FIG. 2A). The close fit of outer perimeter of plunger body 160 to inner perimeter of body 112, in conjunction with a seal 370 (see, FIGS. 3B-3C), provides sufficient suction through dispense opening 135 when plunger 150 is moved away from tip portion 130 so that liquid medicament is drawn in through dispense opening 135. Thus, a user merely draws plunger 150 away from tip portion 130 until second end 173 of plunger grip portion 170 is aligned with the desired dosage marker 120 to ensure that the correct dosage of medicament has been drawn into syringe 100. Preferably, dosage markings 120 can be configured to conform to the shape of seal 370 to assist the user in seeing the dose of medicament withdrawn and to be dispensed.

The substantially oval body 112 of barrel 110 has a major axis that can range from about 1 cm to about 4 cm, preferably about 1.5 cm to about 2.5 cm, more preferably from about 1.75 cm to about 2.25 cm, and most preferably about 2 cm. The minor axis can range from about 0.5 cm to about 2.5 cm, preferably about 0.75 cm to about 2.0 cm, more preferably from about 1.0 cm to about 1.75 cm, and most preferably about 1.5 cm. The ratio of major axis dimension to minor axis dimension can have an aspect ratio of major axis:minor axis that ranges from about 4:1 to about 1.25:1, preferably from about 3:1 to about 1.5:1, more preferably 2:1 to about 1.5:1, and most preferably from about 1.5:1 to about 1.25:1. These aspect ratios will provide an oval body 112 that is not susceptible to rolling or tipping longitudinally or along the longitudinal length thereof, thus ensuring that tip portion 130 will remain above and not contact any surface or substrate upon which syringe 100 is placed. Also, these aspect ratios provide a size and shape to syringe 100 that is comfortable to hold by a user in one hand. In addition, the aspect ratio of the oval shape provides a good seal in the body of the syringe while, at the same time, provides an ergonomic form that handles well and feels comfortable to the user. Thus, the oval form provides a balance between ergonomics and sealing capability that is not provided by circular syringe bodies.

The overall length of body 112 can range from about 8 cm to about 15 cm, preferably from about 9 cm to about 13 cm, more preferably from about 10 cm to 12 cm, and most preferably from about 11 cm to about 12 cm. The overall length of dispense opening 135 can range from about 0.3 cm to about 0.8 cm, preferably from about 0.4 cm to about 0.7 cm, more preferably from about 0.4 cm to about 0.6 cm, and most preferably about 0.5 cm. The set of substantially evenly spaced dose markings 120 generally comprise markings of 0.5 mL to about 1.0 mL of dosage amount between each pair of markings.

In the preferred embodiment shown in the Figures, the width F-F (see, e.g., FIG. 3A1) of plunger grip portion 170 is sized larger than the width of body slot 114 so that the lateral edges 174 of plunger grip portion 170 are supported by lateral edges 116 of body slot 114 as shown in 3A1 of FIG. 3. However, as will be appreciated by those of skill in the art, the width of plunger grip portion 170 does not necessarily need to be wider than the width of body slot 114. This is, in part, due to the presence of connection 175 that supports one end of plunger grip portion 170. In an alternate embodiment according to the present disclosure, plunger grip portion 170 can be the same width as the body slot 114, or narrower than body slot 114. Since during use plunger grip portion 170 is generally inserted at least some distance into body 112, second end 173 of plunger grip portion 170 will rest on the upper surface of body 112 in the area of dosage marker(s) 120. Therefore, there is no requirement for plunger grip portion 170 to have a width greater than body slot 114.

Referring to FIGS. 3A-3C, the alignment of second end 173 of plunger grip portion 170 at various dosage markers 120 for providing different doses of medicament is shown. As shown at 3A1 in FIG. 3A, plunger 150 is disposed as far as possible into body slot 114 of body 112 of syringe 100 so that plunger tip 165 is fully inserted into tip 130 of tip portion 130 of body 112. The outer perimeter of plunger tip 165 meets and seals against inner perimeter of tip portion 130 at interface 310. In this position, plunger tip 165, shown clearly in FIG. 3A1, is substantially aligned and flush with dispense opening 135. As indicated at arrow 320, second end 173 of plunger grip portion 170 is disposed at dosage marker "0", indicating that 0 mL of medicament has been drawn into syringe 100. In 3A2 of FIG. 3A, plunger 150 has been moved away from tip portion 130 and second end 173 of plunger grip portion 170 is aligned with a dosage marker 120 indicating that 3.5 mL of medicament have been drawn into syringe 100, as indicated by arrow 330. In 3A3 of FIG. 3A, plunger 150 has been drawn away from tip portion 130 and second end 173 of plunger grip portion 170 is aligned with a dosage marker 120 indicating that 7.0 mL of medicament have been drawn into syringe 100 as indicated by arrow 340. As will be appreciated by those of skill in the art, because body slot 114 has a length E-E, shown in FIG. 2A, that is approximately half the length of body 112, drawing plunger 150 beyond dosage marker 120 indicating a dose of 7.0 mL, will break the vacuum provided by the close fit of outer perimeter of plunger body 160 and seal 370 to inner dimension of body 112. To avoid drawing plunger 150 beyond dosage marker 7.0 mL, a "stop", such as in the form of a protrusion, can be placed on the inside of body 112. Stops of this type are of common use and design in syringes such as disclosed herein. Preferably, an indicator or marking showing "mL" can be placed on or near second end 173 of plunger grip portion 170 to assist the user in knowing what dosage of medicament has been withdrawn into body 112.

FIGS. 3B and 3C show a preferred embodiment of plunger 150 according to the present disclosure. FIG. 3B is a preferred configuration of second end 173 of plunger grip portion 170. Second end 173 of plunger grip portion 170 has a semicircular window 350. In use, semicircular window 350 displays the dosage number (3.0 mL shown by arrow 360 in FIG. 3B) and serves as a second indicator, in addition to second end 173 of plunger grip portion 170 aligning with dosage marker 120, of the dosage of medicament drawn into syringe 100. FIGS. 3B and 3C also show a third indicator of the dosage of medicament selected by a user. Seal 370 disposed on plunger body 160 proximal to plunger tip 165 can be colored and aligns with second end 173 of plunger grip portion 170. Seal 370, when colored, can be better seen through transparent body 112. Seal 370 acts as a third indicator of the dosage of medicament selected by a user along with second end 173 of plunger grip portion 170 and semicircular window 350. As mentioned above, dosage markings 120 can be configured to conform to the shape of seal 370 to assist the user in seeing the dose of medicament withdrawn or to be dispensed. Also, it is preferable that the numbers for dosage markings 120 be imprinted/embossed onto a flat area of barrel 120 in order to be so that they are less subject to contacting window 350 or any portion of plunger grip portion 170. By this configuration, dosage markings 120 are less subject to being worn away and, thus, difficult to see. Of course, all or only one such indicator can be used, according to design and manufacturing choice. As shown in the preferred embodiment of FIGS. 3B and 3C, seal 370 is colored to enhance its visibility through transparent body 112. However, even without any color, seal 370 will provide a line of contrast between the portions of body 112 filled with medicament and the portions of body 112 that are unfilled. Thus, as noted, providing a colored seal 370 is merely a preferred embodiment of the present disclosure. In contrast to the state of the art in which seals on known syringes typically lie "flat" around the circumference or outer perimeter of the plunger, seal 370 of the present disclosure has been shaped into a curved profile. This curved profile allows seal 370 to align with the shape of the dosage marker(s) 120 and second end 173 of plunger grip portion 170. This curve of seal 370 creates the aforementioned line of contrast between the filled and un-filled portions of body 112 and mirrors the shape of dosage marker(s) 120. This provides a very clear indication to the user of the location where plunger 160 lies on the dosage marker 120 scale.

Also preferably, the second end of the plunger grip portion 170 can have a protrusion 174, shown in FIG. 3C, disposed facing surface 119 of barrel 110 or body 112 so that protrusion 174 interacts with the raised dosage markings 120 to provide an auditable and/or tactile "click" that serves to ensure that the user has drawn the correct dosage into and through the substantially circular fill and dispense opening 135. This feature is particularly useful when a user is operating syringe 100 in the dark and does not wish to put on the light, for example when administering oral analgesics to a young child.

Figure 4A:
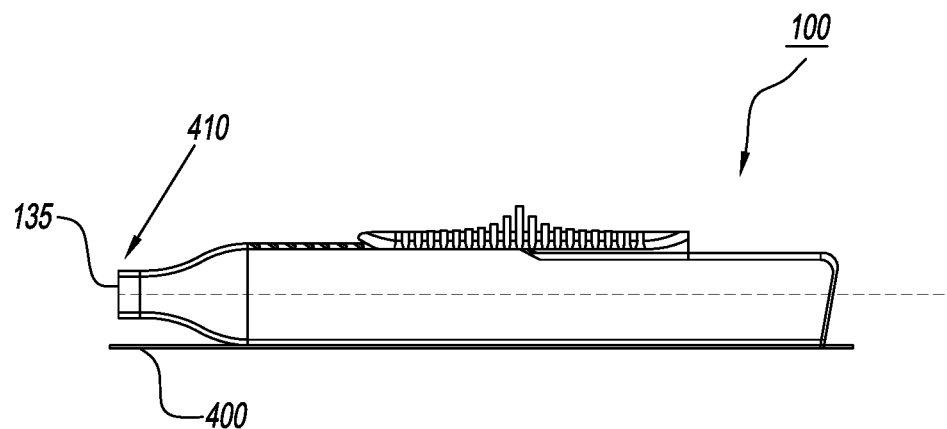
FIG. 4A is a side perspective view of the syringe of FIG. 1 when laid on a surface.

Referring to FIG. 4A, syringe 100 has been placed on a surface 400. The oval shape of body 112 prevents syringe 100 from rolling on surface 400 and maintains substantially circular fill and dispense opening 135 away from surface 400. In FIG. 4A, substantially circular fill and dispense opening 135 is shown as clearly disposed above surface 400 as is indicated at 410.

Figure 4B:
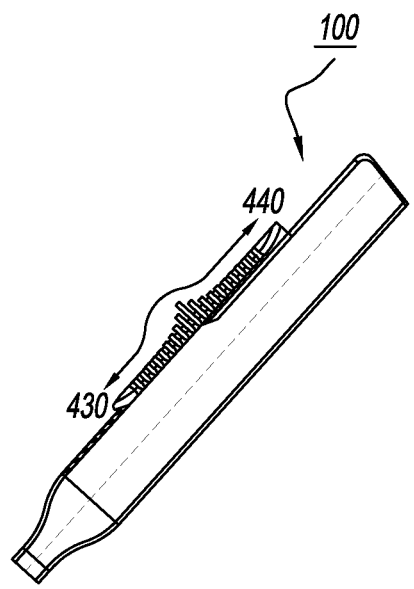
FIG. 4B is a side perspective view of the syringe of FIG. 1 when in a medicament withdrawing or dispensing position.

FIG. 4B shows syringe 100 in fill and/or dispense position. Arrows 430 and 440 point toward distal end 124 and proximal end 122, respectively, of body 112. As envisioned by one of skill in the art, a user placing his or her finger, e.g., thumb, on the proximal side of approximate center 172 of plunger grip portion 170 can easily push plunger 150 toward distal end 124 of body 112 to dispense a medicament due to the height and placement of ridges 180. Likewise, to draw a medicament into syringe 100, a user places a finger, e.g., thumb, on the distal side of approximate center 172 of plunger grip portion 170 and can easily pull plunger 150 away from distal end 124 of body 112 and toward proximal end 122 of body 112.

Accordingly, various embodiments and alternatives of an ergonomic syringe improve and facilitate the withdrawal and dispensing of medicaments. By way of illustration, the disclosed embodiments allow for one-handed operation and facilitate a user's ability to stabilize the syringe when in use. The syringe have an exterior shape that more comfortably fits a user's hand and prevents rolling of the syringe when placed on a surface. In addition, due to the exterior shape of the syringe, the injection tip will not touch a surface when the syringe is placed thereon. This provides improved hygiene and reduced contamination of the syringe tip.

While the present disclosure has been described with reference to one or more exemplary embodiments, it will be understood by those skilled in the art that various changes may be made and equivalents may be substituted for elements thereof without departing from the scope of the present disclosure. In addition, many modifications may be made to adapt a particular situation or material to the teachings of the disclosure without departing from the scope thereof. Therefore, it is intended that the present disclosure not be limited to the particular embodiment(s) disclosed as the best mode contemplated, but that the disclosure will include all embodiments falling within the scope of the appended claims.

What is claimed is:

1. A syringe comprising:
a body having a hollow interior, the body comprising:
a substantially oval barrel having a major axis and a perpendicular minor axis, wherein the barrel has a length between a proximal end and a distal end;
a body tip portion, wherein the body tip portion tapers from the distal end to a substantially circular fill and dispense opening;
a body slot in the barrel along a longitudinal axis of the barrel, wherein the body slot has a length that begins at the proximal end and ends towards the distal end about one-half the length of the barrel, and wherein the body slot has a width that is smaller than the major axis and is approximately centrally disposed perpendicular to the minor axis,
wherein the body has a portion, extending from the distal end to the body slot, that is a remainder of the body, wherein the portion is integrally formed and contiguous with the tip portion,
wherein the barrel has a set of substantially evenly spaced dose markings on a surface of said portion,
wherein the dose markings are disposed substantially in alignment with the body slot; and
a plunger comprising:
a substantially oval plunger body having a proximal end and a distal end, wherein the plunger body has an exterior shape and dimensions that correspond to the hollow interior of the barrel;
a plunger tip portion that is at the distal end of the plunger body and tapers to correspond to the cross-section of body tip portion, wherein the plunger tip portion ends approximately at the dispense opening; and
a plunger grip portion having a proximal end and a distal end, wherein the plunger grip portion is connected to the plunger body, and wherein the plunger grip portion is disposed in association with the body slot.

2. The syringe of claim 1, wherein the plunger grip portion has a width that is sized larger than the width of the body slot.

3. The syringe of claim 1, wherein the plunger grip portion is configured to correspond to the set of dose markings on the surface of the barrel.

4. The syringe of claim 1, wherein the plunger grip portion has a set of substantially evenly spaced ridges disposed on an upper surface thereof to provide a surface against which a user can push and pull with a finger.

5. The syringe of claim 1, wherein the plurality of substantially evenly spaced dosage markings are raised, and wherein the plunger grip portion has a protrusion that interacts with the raised dosage markings to provide an auditable and/or tactile "click" as the protrusion passes over each dosage marking.

6. The syringe of claim 1, wherein the plunger grip portion has a window at the distal end.

7. A method of producing a syringe having a syringe body having a hollow cross-section and a plunger, the method comprising:
providing the body with a substantially oval barrel having a major axis and a perpendicular minor axis, wherein the barrel has a length between a proximal end and a distal end;
providing a body slot disposed in the barrel along the longitudinal axis, wherein the body slot has a length and a width, wherein the length is from the proximal end towards the distal end for about one-half the length of the barrel, wherein the width is smaller than the major axis, and wherein the body slot is approximately centrally disposed perpendicularly to the minor axis;
providing a body tip portion that tapers from the distal end of the barrel to a substantially circular fill and dispense opening;
providing the plunger with a substantially oval plunger body having a proximal end and a distal end, wherein the plunger body is provided with exterior dimensions that correspond to the hollow cross-section of the substantially oval barrel;
providing the plunger body with a plunger tip disposed at the distal end of the plunger body, wherein the plunger tip is provided with a tapering dimension so as to correspond to the hollow cross-section of body tip portion, and wherein the plunger tip is provided so as to end substantially at the dispense opening of the barrel;
providing a plunger grip portion having a proximal end and a distal end, wherein the plunger grip portion is connected to the plunger body, and wherein the plunger grip portion is disposed in association with the body slot;
providing the body with a portion, extending from the distal end to the body slot, that is a remainder of the body, wherein the portion is integrally formed and contiguous with the tip portion, providing the barrel with a set of substantially evenly spaced dose markings on a surface of said portion,
wherein the dose markings are disposed substantially in alignment with the body slot.

8. The method of producing a syringe according to claim 7, further comprising providing the plunger grip with a width that is sized larger than the width of the body slot.

9. The method of producing a syringe according to claim 7, further comprising providing the plunger grip with a set of substantially evenly spaced ridges disposed on an upper surface of the plunger grip to provide a surface against which a user can push and pull with a finger.

10. The method of producing a syringe according to claim 7, further comprising providing the barrel with a plurality of substantially evenly spaced dosage markings between the body tip portion and the body slot.

11. The method of producing a syringe according to claim 10, further comprising providing the barrel with a plurality of raised substantially evenly spaced dosage markings.

12. The method of producing a syringe according to claim 11, further comprising providing the plunger grip with a protrusion that interacts with the raised dosage markings to provide an auditable and/or tactile "click" as the protrusion passes over each dosage marking.

13. The method of producing a syringe according to claim 8, further comprising providing the plunger grip portion with window at the distal end.

14. The syringe of claim 1, wherein the plunger grip portion has a longitudinal axis with a first portion thereof attached to the plunger and is adapted to fit in the body slot, and a second portion configured to be disposed above the outer surface of the barrel body along the body slot or opening.

15. The method of producing a syringe according to claim 7, further comprising providing the plunger grip having a length and a width, with a first end of the length of the plunger grip attached to the proximal end of the plunger body, and a second end of the length of the plunger grip configured to be disposed above the surface of the barrel.

16. The method of producing a syringe according to claim 14, further comprising providing the plunger grip, sized so that a part of the plunger grip remains disposed above the body slot.

17. The syringe of claim 1, wherein the plunger grip portion is sized larger than the width of body slot, so that lateral edges of the plunger grip portion are supported by later edges of the body slot.

* * * * *